United States Patent
Hazan (10) Patent No.: US 10,559,080 B2
(45) Date of Patent: Feb. 11, 2020

(54) ADAPTIVE SEGMENTATION OF LESIONS IN MEDICAL IMAGES

(71) Applicant: International Business Machines Corporation, Armonk, NY (US)

(72) Inventor: Alon Hazan, Zichron Yaacov (IL)

(73) Assignee: International Business Machines Corporation, Armonk, NY (US)

(*) Notice: Subject to any disclaimer, the term of this patent is extended or adjusted under 35 U.S.C. 154(b) by 103 days.

(21) Appl. No.: 15/854,822

(22) Filed: Dec. 27, 2017

(65) Prior Publication Data
US 2019/0197682 A1 Jun. 27, 2019

(51) Int. Cl.
*G06T 7/00* (2017.01)
*G16H 30/40* (2018.01)
*G06T 7/11* (2017.01)
*G06T 7/155* (2017.01)
*G06K 9/46* (2006.01)
*G06K 9/62* (2006.01)

(52) U.S. Cl.
CPC .............. *G06T 7/0012* (2013.01); *G06K 9/46* (2013.01); *G06K 9/6267* (2013.01); *G06T 7/11* (2017.01); *G06T 7/155* (2017.01); *G16H 30/40* (2018.01); *G06T 2200/04* (2013.01); *G06T 2207/30096* (2013.01)

(58) Field of Classification Search
CPC ......... G06T 7/0012; G06T 7/11; G06T 7/155; G06T 2200/04; G06T 2207/30096; G06K 9/46; G06K 9/6267; G16H 30/40
See application file for complete search history.

(56) References Cited

U.S. PATENT DOCUMENTS

| 6,081,612 | A | * | 6/2000 | Gutkowicz-Krusin ..... A61B 5/0071 382/128 |
| 7,418,123 | B2 | | 8/2008 | Giger et al. |
| 2010/0087756 | A1 | * | 4/2010 | Egorov ............ A61B 5/0053 600/587 |
| 2010/0189319 | A1 | | 7/2010 | Wu et al. |
| 2014/0148679 | A1 | | 5/2014 | Eary et al. |
| 2015/0087957 | A1 | * | 3/2015 | Liu ...................... G06T 7/42 600/408 |
| 2015/0356730 | A1 | | 12/2015 | Grove et al. |
| 2016/0022238 | A1 | | 1/2016 | Park |

FOREIGN PATENT DOCUMENTS

CN 104715483 6/2015

OTHER PUBLICATIONS

Nie et al., "Quantitative Analysis of Lesion Morphology and Texture Features for Diagnostic Prediction in Breast MRI", Academic Radiology, Dec. 2008, pp. 1513-1525, vol. 15, Issue 12.

\* cited by examiner

*Primary Examiner* — Leon Flores
(74) *Attorney, Agent, or Firm* — Dvir Gassner (57) ABSTRACT

A method comprising using at least one hardware processor for: receiving a digital medical image and a binary image mask, wherein the binary image mask depicts a segmentation of a lesion in the digital medical image; computing a plurality of layers of the lesion; for each of the plurality of layers of the lesion, extracting layer features; and sending the extracted layer features to a lesion classifier.

14 Claims, 5 Drawing Sheets

ADAPTIVE SEGMENTATION OF LESIONS IN MEDICAL IMAGES

BACKGROUND

The invention relates to the field of medical imaging.

Medical imaging may be used to capture digital images of tumors, and the tumor objects in the digital image identified, such as by defining and/or calculating a binary image mask with one value for the tumor object, such as 1, 255, −1, or the like, and a second value for the background, such as 0, −1, 255, or the like. The identified tumor image (digital image and mask) may be further processed to compute features of the tumor, such as mean intensity, relative intensity, entropy, texture, and/or the like, that in turn can be used to classify the tumor. The tumor classification is important for diagnosis, prognosis, treatment, and/or the like.

Machine learning techniques may be applied to identified tumors, where a training set is used to develop extraction methods for feature extraction. The extraction methods are used to extract features from a patient's tumor image. For example, computer vision texture analysis tools are used to extract features from a tumor image.

For example, oriented gradients are used to extract features from tumor images, as described by Dalal et al. in "Histograms of Oriented Gradients for Human Detection" published in the proceedings of IEEE Computer Society Conference on Computer Vision and Pattern Recognition, 2005, San Diego, Calif., USA (DOI: 10.1109/CVPR.2005.177). For example, wavelet-based textures are used to extract features from tumor images, as described by Do et al. in "Wavelet-based texture retrieval using generalized Gaussian density and Kullback-Leibler distance" published in IEEE transactions on image processing, 2002, volume: 11, Issue: 2, page(s): 146-158 (DOI: 10.1109/83.982822). For example, grey level co-occurrence matrices are used to extract features from tumor images, as described by Haralick et al. in "Textural Features for Image Classification", published in IEEE Transactions on Systems, Man, and Cybernetics, Vol. SMC-3, 1973, pp. 610-621 (DOI: 10.1109/TSMC.1973.4309314). For example, deep neural networks are used to extract features from tumor images, as described by Krizhevsky et al. in "Imagenet classification with deep convolutional neural networks" published in the proceedings of Proceedings of the 25th International Conference on Neural Information Processing Systems—Volume 1, 2012, Pages 1097-1105.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

There is provided, in accordance with an embodiment, a method comprising using at least one hardware processor for receiving a digital medical image and a binary image mask, wherein the binary image mask depicts a segmentation of a lesion in the digital medical image. The hardware processor(s) are used for computing a plurality of layers of the lesion. The hardware processor(s) are used, for each of the plurality of layers of the lesion, extracting layer features. The hardware processor(s) are used for sending the extracted layer features to a lesion classifier.

There is provided, in accordance with an embodiment, a computer program product for lesion feature extraction, the computer program product comprising a non-transitory computer-readable storage medium having program code embodied therewith. The program code executable by at least one hardware processor to receive a digital medical image and a binary image mask, wherein the binary image mask depicts a segmentation of a lesion in the digital medical image. The program code executable by at least one hardware processor to compute a plurality of layers of the lesion. The program code executable by at least one hardware processor to for each of the plurality of layers of the lesion, extract layer features. The program code executable by at least one hardware processor to send the extracted layer features to a lesion classifier.

There is provided, in accordance with an embodiment, a system for lesion feature extraction, comprising at least one hardware processor. The system comprises a non-transitory computer-readable storage medium comprising program code embodied therewith. The program code executable by the at least one hardware processor to receive a digital medical image and a binary image mask, wherein the binary image mask depicts a segmentation of a lesion in the digital medical image. The program code executable by the at least one hardware processor to compute a plurality of layers of the lesion. The program code executable by the at least one hardware processor to, for each of the plurality of layers of the lesion, extract layer features. The program code executable by the at least one hardware processor to send the extracted layer features to a lesion classifier.

In some embodiments, the plurality of layers of the lesion are computed by iteratively performing a morphological erosion of the binary image mask, and subtraction of the mask from the binary image mask of the previous iteration.

In some embodiments, a seed used in the morphological erosion is at least one of isotropic, anisotropic, constant size across iterations, different size for each iteration, constant size over the surface of the lesion, different size over the surface of the lesion, constant size throughout the volume of the lesion, different size throughout the volume of the lesion, and variable size according to the distance to the original lesion surface.

In some embodiments, the plurality of layers of the lesion are computed by iteratively segmenting a plurality of surface voxels from the binary image mask and adjacent surface voxels to form the plurality of layers.

In some embodiments, the digital medical image is a two-dimensional (2D) medical image and the plurality of layers are 2D annular regions following an edge of the lesion.

In some embodiments, the digital medical image is a three-dimensional (3D) medical image and the plurality of layers are 3D shells following a surface of the lesion.

In some embodiments, the plurality of layers of the lesion are computed by (i) computing a center of mass of the digital medical image, (ii) tracing a plurality of rays from the center of mass to the edge of the binary image mask, (iii) marking an equal number of ray segments for each of the plurality of rays, (iv) creating layers by drawing a layer boundary through the ends of each ray segment across the plurality of rays.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

DETAILED DESCRIPTION

Disclosed herein are methods, systems, and computer program products for calculating features of neoplasms, such as masses, tumors, lesions, and/or the like, from medical digital images, such as ultrasound images, mammograms, MRI (Magnetic Resonance Imaging) images, CT (Computerized Tomography) images, and/or the like. For convenience, the term "lesion" is used herein to refer to a cancerous growth, or neoplasm.

A medical digital image is received together with a binary digital image mask identifying the pixels/voxels depicting one or more lesions in the digital image. As used herein, the term "image" means a digital image and the term "voxel" means "pixel" or "voxel", depending on whether the image is two-dimensional (2D) or three-dimensional (3D). Each lesion is processed separately. By segmenting the lesion in the image into layers and then extracting features for each layer, the features contain information on the lesion as a layered object which significantly improves a subsequent tumor classification process.

Many conventional solutions regard the entire lesion as a single growth, and thus have limited information on the structure of the lesion as a layered object.

When calculating the features of a lesion that appears in a medical image (i.e. ultrasound, mammogram, MRI, etc.), the lesion is segmented it into layers of approximately equal thickness. The segmentation may be computed by repeated morphologic erosion of the binary image mask, and subtraction of the resulting eroded mask from the previous binary mask, thus identifying the voxels of the layer. Each layer retains the overall structure of the lesion, like peeling an onion layer by layer.

Optionally, when the medical image is a two-dimensional (2D) medical image the layers are annular regions of pixels on the 2D image.

Optionally, when the medical image is a three-dimensional medical image the layers are shell regions of voxels on the 3D image.

As used herein, the use of 2D and 3D terminology is interchangeable, and inherently tied to the dimensionality of the medical image and binary image mask.

Once the segmentation to layers has been computed, textural (or other) features are computed for each layer, instead of on the whole lesion. This process will produce a number of features multiplied by the number of layers, and thus provide a better description of the lesion.

Figure 1:
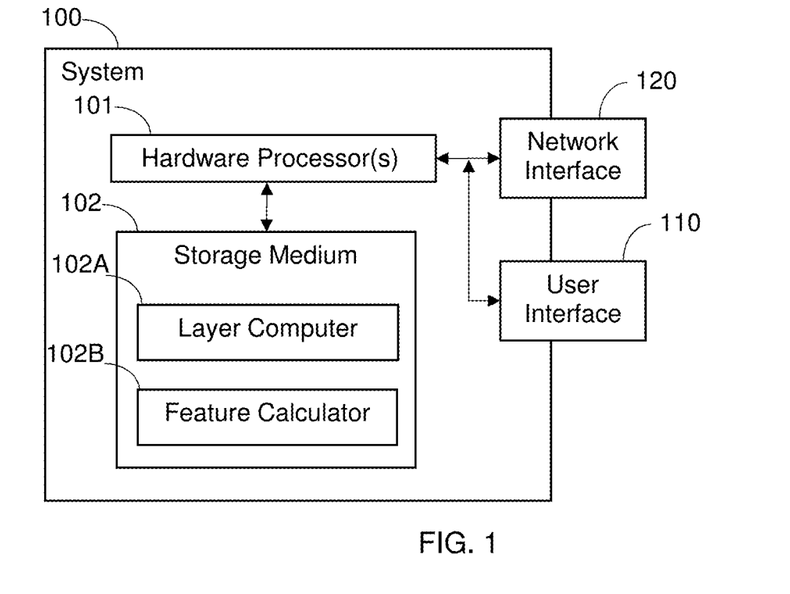
FIG. 1 shows schematically a system for segmentation of a lesion into layers.

Reference is now made to FIG. 1, which shows schematically a system 100 for segmentation of a lesion into layers. System 100 comprises one or more hardware processors 101, a non-transitory computer readable storage medium 102, a user interface 110, and a network interface 120. Storage medium 102 comprises software, such as program code configured to execute on hardware processor(s) 101, including a Layer Computer 102A that receives a 3D digital image and a binary image mask and a Feature Calculator 102B that calculates features for two or more layers computed from the binary mask. Since most conventional feature calculators calculate features for a single lesion, the program code of Feature Calculator 102B may be configured to separate the layers and calculate each layer separately, then combine the features for all layers into an output sent to another module/computer for further processing, such as to classify the lesion.

Figure 2:
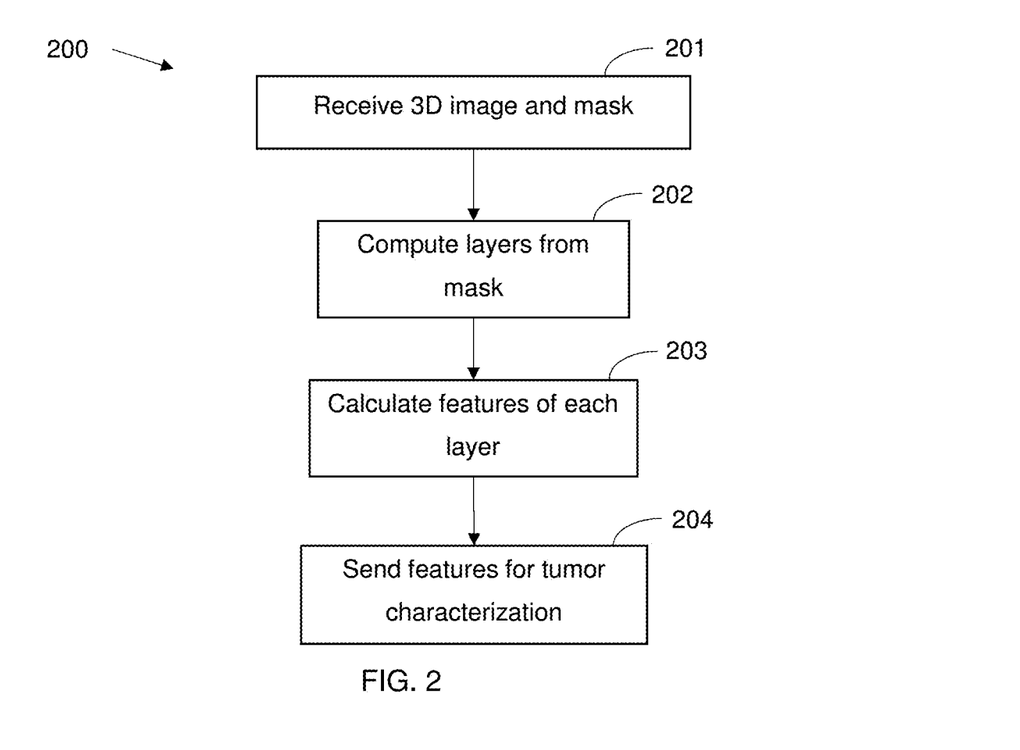
FIG. 2 shows a flowchart of a method for segmentation of a lesion into layers.

Reference is now made to FIG. 2, which shows a flowchart of a method 200 for segmentation of a lesion into layers. Method 200 includes an action of receiving 201 a 3D image and a binary image mask, where both may be in digital format. Method 200 includes an action of computing 202 two or more layers from the mask. Method 200 includes an action of calculating 203 features of the lesion for each layer. Method 200 includes an action of sending 204 the features for tumor characterization.

Figure 3:
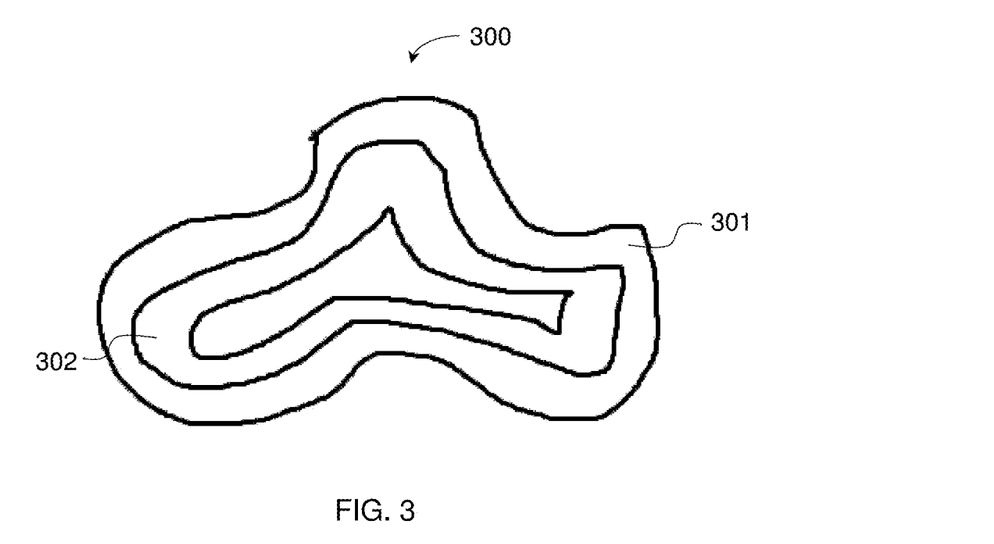
FIG. 3 shows schematically a segmentation of a lesion into layers.

Reference is now made to FIG. 3, which shows schematically a segmentation of a lesion 300 into layers. A first layer 301 may be computed, such as using a morphological erosion on the mask and then subtracting the eroded mask from the original mask. A second layer 302 may be computed by eroding the eroded mask, and subtracting that from the eroded mask. Further layers may be computed similarly, such as in an iterative manner.

Figure 4:
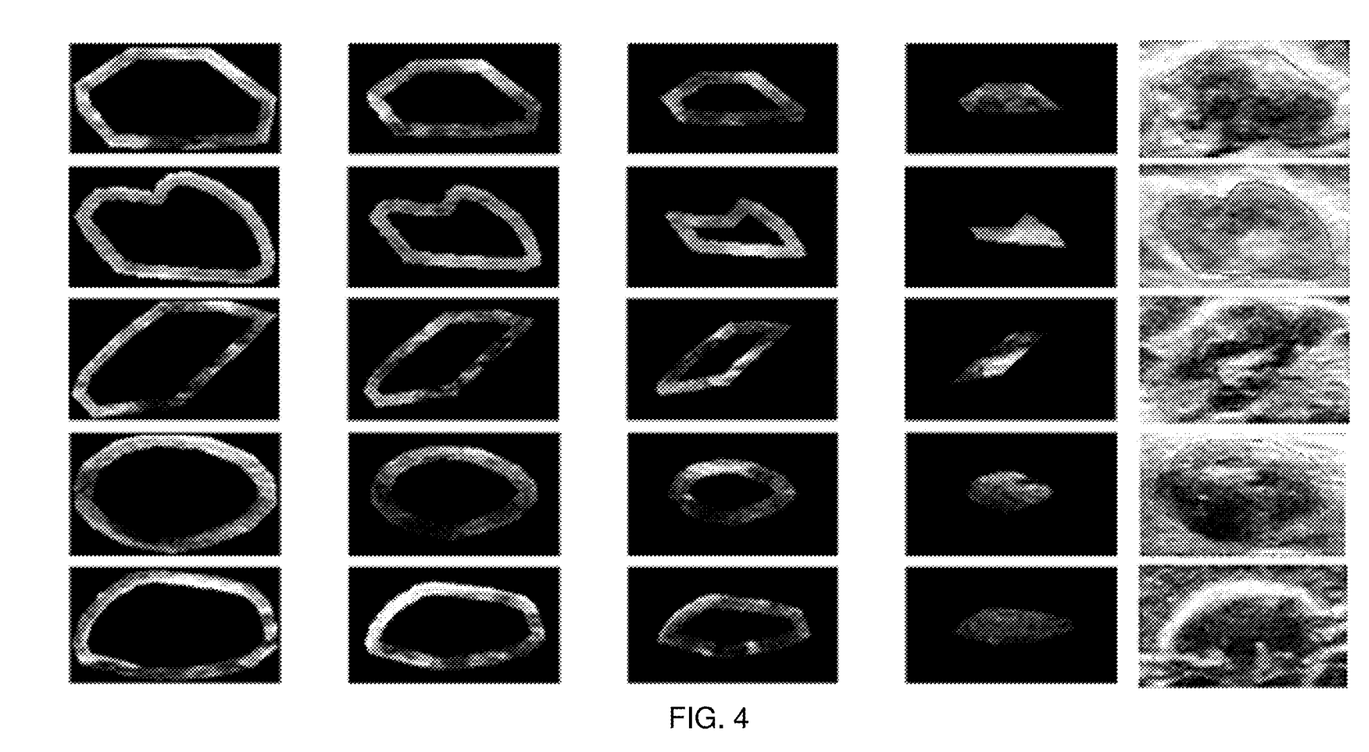
FIG. 4 shows an array of tumor images each segmented into layers.

Reference is now made to FIG. 4, which shows an array of tumor images each segmented into layers. Each of the five rows is a different ultrasound lesion, with the left column showing the outer layer of the lesion, going to the core of the lesion. The right most column is the complete tumor image with outer boundary marked. The layers were calculated using morphological operators of erosion and dilation.

Figure 5:
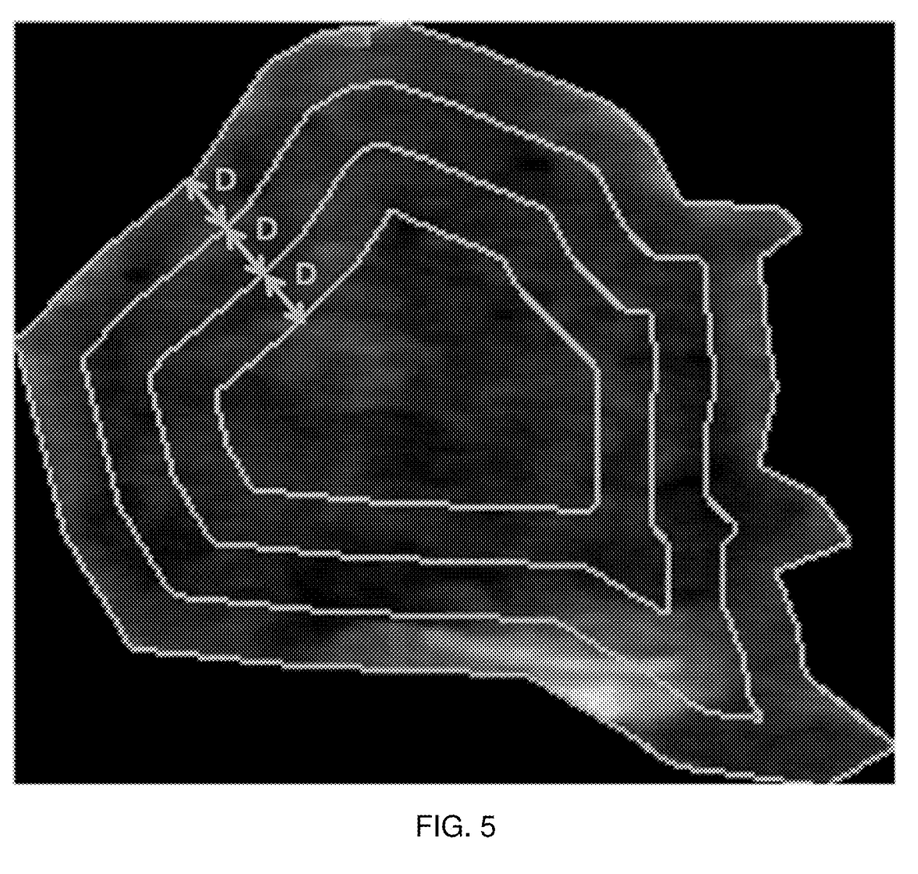
FIG. 5 shows a tumor image segmented into layers using morphological erosion.

Reference is now made to FIG. 5, which shows a tumor image segmented into layers using morphological erosion. Each erosion operation removes a layer of thickness D.

Figure 6:
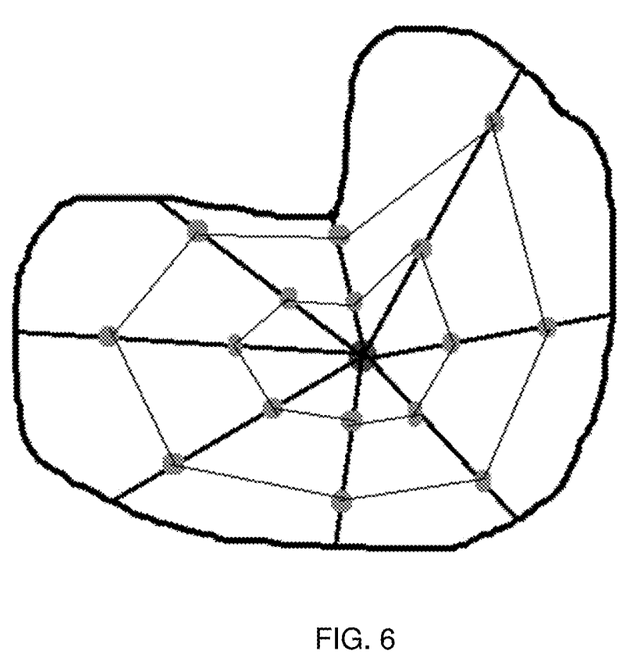
FIG. 6 shows schematically a segmentation of a lesion into layers using ray tracing.

Reference is now made to FIG. 6, which shows schematically a segmentation of a lesion into layers using ray tracing.

The layers were segmented by computing the center of mass of the lesion, stretching rays from the center, and segmenting each ray to equal number of segments to create layer waypoints. The waypoints may be connected, and the resulting polygon smoothed, such as using a b-spline function, to locate the boundaries of the layers. The number of rays may determine the accuracy of the layers.

Optionally, external layers to the tumor are evaluated in addition to the internal layers. The features of the surrounding tissue to the tumor may be significant for classification of the tumor. In such cases, one or more layers around the lesion may be selected using the morphological operators (i.e. erosion, dilation, opening, closing, and/or the like) or the ray tracing embodiment.

Layered features may improve the tumor classification of the lesion as a whole, by quantifying the inner feature complexity of the lesion. For example, measuring homogeneity value of the lesion can be 0.8 (i.e. on a 0-1 scale) while the homogeneity of each layer separately may vary (e.g. 0.2, 0.9, 0.6, etc.). Looking at the homogeneity value of each layer may give a more detailed evaluation of the lesion than looking at the homogeneity value of the whole lesion. Other measures, such as wavelets, texture, gray-level co-occurrence matrix, plain size, deep neural network features, and/or the like may also provide improved lesion characterization when computed for layers. Each different feature value for each different layer (assuming that each lesion is segmented with the same number of layers) may be a feature to help differentiate one lesion from another in a meaningful way.

For example, plain size quantifies the characteristics of an image patch, one of those characteristics may be the size/area/volume of the patch in terms of number of pixels/voxels it contains, and their grey scale values. In the medical field, the pixel size is translated to physical size (microns) allowing an understanding of the real-world size of tumors or other imaged elements, and this may be essential to understanding severity and classification of lesions.

As lesions are often cancerous objects, they usually grow bigger over time, starting from some center and growing outwards. That is why layer segmentation may quantify the age and/or growth of the tissue. The core is usually the oldest cancerous tissue and the outer layer is the younger tissue.

An example application of segmenting tumor layers, is a cascaded detector-classifier module where during the first step the detector is an algorithm for segmentation of the tumor, such as an artificial neural network, computer vision segmentation, and/or the like. The layer segmentation may use a mediator module, such that a classifier will have the metrics for each layer, such as a classification algorithm based on neural networks and/or the like.

Another example application is a convolutional neural network classifier, where the layer segmentation is applied prior to classification. The feature space, such as parameter values, may be the representation of the image after calculating a convolutional neural network for multiple layers of the tumor. In that feature space, the image may be transformed into a tensor of size (x,y,c) where x,y are proportional to the original image dimensions and c is the number of channels as defined by the network architecture. Each pixel in the original image now corresponds to a depth vector of length c, which has "features" (i.e. parameter values) for that pixel. Using the layer segmentation technique, statistics of features from all pixels in each layer (such as average, mean, variance) may be calculated separately. The resulting vectors for a layer may propagate to the next layer of the network, thereby providing additional information on the tumor.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire. Rather, the computer readable storage medium is a non-transient (i.e., not-volatile) medium.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising using at least one hardware processor for:
   receiving a digital medical image and a binary image mask, wherein the binary image mask depicts a segmentation of a lesion in the digital medical image;
   computing a plurality of layers of the lesion, wherein the computing is selected from the group consisting of:
   (a) computing the plurality of layers iteratively, wherein:
      a first iteration comprises performing morphological erosion of the binary image mask, and subtracting the eroded binary image mask from the binary image mask, and
      each following iteration comprises performing additional morphological erosion of the eroded binary image mask of the previous iteration, and subtracting the additionally-eroded binary image mask from the eroded binary image mask of the previous iteration,
   (b) computing the plurality of layers by ray tracing, comprising:
      computing a center of mass of the digital medical image,
      tracing a plurality of rays from the center of mass to the edge of the binary image mask,
      marking an equal number of ray segments for each of the plurality of rays, and
      creating layers by drawing a layer boundary through the ends of each ray segment across the plurality of rays;
   for each of the plurality of layers of the lesion, extracting layer features; and
   sending the extracted layer features to a lesion classifier.

2. The method according to claim 1, wherein a seed used in the morphological erosion is at least one of: isotropic, anisotropic, constant size across iterations, different size for each iteration, constant size over the surface of the lesion, different size over the surface of the lesion, constant size throughout the volume of the lesion, different size throughout the volume of the lesion, and variable size according to the distance to the original lesion surface.

3. The method according to claim 1, wherein the plurality of layers comprise at least one external layer computed outside the binary image mask.

4. The method according to claim 1, wherein the digital medical image is a two-dimensional (2D) medical image and the plurality of layers are 2D annular regions following an edge of the lesion.

5. The method according to claim 1, wherein the digital medical image is a three-dimensional (3D) medical image and the plurality of layers are 3D shells following a surface of the lesion.

6. A computer program product for lesion feature extraction, the computer program product comprising a non-transitory computer-readable storage medium having program code embodied therewith, the program code executable by at least one hardware processor to:
   receive a digital medical image and a binary image mask, wherein the binary image mask depicts a segmentation of a lesion in the digital medical image;
   compute a plurality of layers of the lesion, wherein the computing is selected from the group consisting of:
   (a) computing the plurality of layers iteratively, wherein:
      a first iteration comprises performing morphological erosion of the binary image mask, and subtracting the eroded binary image mask from the binary image mask, and
      each following iteration comprises performing additional morphological erosion of the eroded binary image mask of the previous iteration, and subtracting the additionally-eroded binary image mask from the eroded binary image mask of the previous iteration,
   (b) computing the plurality of layers by ray tracing, comprising:

computing a center of mass of the digital medical image, tracing a plurality of rays from the center of mass to the edge of the binary image mask, marking an equal number of ray segments for each of the plurality of rays, and creating layers by drawing a layer boundary through the ends of each ray segment across the plurality of rays;

for each of the plurality of layers of the lesion, extract layer features; and send the extracted layer features to a lesion classifier.

7. The computer program product according to claim 6, wherein a seed used in the morphological erosion is at least one of: isotropic, anisotropic, constant size across iterations, different size for each iteration, constant size over the surface of the lesion, different size over the surface of the lesion, constant size throughout the volume of the lesion, different size throughout the volume of the lesion, and variable size according to the distance to the original lesion surface.

8. The computer program product according to claim 6, wherein the plurality of layers comprise at least one external layer computed outside the binary image mask.

9. The computer program product according to claim 6, wherein the digital medical image is a two-dimensional (2D) medical image and the plurality of layers are 2D annular regions following an edge of the lesion.

10. The computer program product according to claim 6, wherein the digital medical image is a three-dimensional (3D) medical image and the plurality of layers are 3D shells following a surface of the lesion.

11. A system for lesion feature extraction, comprising:

at least one hardware processor;

a non-transitory computer-readable storage medium comprising program code embodied therewith, the program code executable by the at least one hardware processor to:

i) receive a digital medical image and a binary image mask, wherein the binary image mask depicts a segmentation of a lesion in the digital medical image;

ii) compute a plurality of layers of the lesion, wherein the computing is selected from the group consisting of:

(a) computing the plurality of layers iteratively, wherein:

a first iteration comprises performing morphological erosion of the binary image mask, and subtracting the eroded binary image mask from the binary image mask, and each following iteration comprises performing additional morphological erosion of the eroded binary image mask of the previous iteration, and subtracting the additionally-eroded binary image mask from the eroded binary image mask of the previous iteration, (b) computing the plurality of layers by ray tracing, comprising:

computing a center of mass of the digital medical image, tracing a plurality of rays from the center of mass to the edge of the binary image mask, marking an equal number of ray segments for each of the plurality of rays, and creating layers by drawing a layer boundary through the ends of each ray segment across the plurality of rays;

iii) for each of the plurality of layers of the lesion, extract layer features; and iv) send the extracted layer features to a lesion classifier.

12. The system according to claim 11, wherein a seed used in the morphological erosion is at least one of: isotropic, anisotropic, constant size across iterations, different size for each iteration, constant size over the surface of the lesion, different size over the surface of the lesion, constant size throughout the volume of the lesion, different size throughout the volume of the lesion, and variable size according to the distance to the original lesion surface.

13. The system according to claim 11, wherein the digital medical image is a two-dimensional (2D) medical image and the plurality of layers are 2D annular regions following an edge of the lesion.

14. The system according to claim 11, wherein the digital medical image is a three-dimensional (3D) medical image and the plurality of layers are 3D shells following a surface of the lesion.

\* \* \* \* \*